United States Patent [19]

Rosenblatt

[11] Patent Number: 5,469,864

[45] Date of Patent: Nov. 28, 1995

[54] LASER SHIELD

[75] Inventor: Solomon Rosenblatt, Montclair, N.J.

[73] Assignee: Merocel Corporation, Mystic, Conn.

[21] Appl. No.: 391,637

[22] Filed: Feb. 21, 1995

Related U.S. Application Data

[63] Continuation of Ser. No. 32,476, Mar. 16, 1993, abandoned, which is a continuation of Ser. No. 259,790, Oct. 19, 1988, abandoned.

[51] Int. Cl.$^6$ .............................. A61F 5/37; A61F 13/00; A61B 19/00; A61M 16/00
[52] U.S. Cl. ..................... 128/849; 128/846; 128/207.14; 128/207.15
[58] Field of Search ................... 128/207.14, 207.15, 128/207.17, 911, 846, 849

[56] References Cited

U.S. PATENT DOCUMENTS

| | | | |
|---|---|---|---|
| 4,098,728 | 7/1978 | Rosenblatt | 521/141 |
| 4,417,576 | 11/1983 | Baran | 128/207.15 |
| 4,489,722 | 12/1984 | Ferraro et al. | |
| 4,520,814 | 6/1985 | Weeks | 128/303 |
| 4,558,093 | 12/1985 | Hatzenbuhler et al. | |
| 4,601,286 | 7/1986 | Kaufman | 128/132 |
| 4,604,998 | 8/1986 | Bellina | |
| 4,611,588 | 9/1986 | Laptewicz, Jr. et al. | |
| 4,616,641 | 10/1986 | Teeple | |
| 4,632,108 | 12/1986 | Geil | |
| 4,635,625 | 1/1987 | Teeple | |
| 4,658,812 | 4/1987 | Hatzenbuhler et al. | |
| 4,715,366 | 12/1987 | Teeple | |
| 4,735,623 | 4/1988 | Hatzenbuhler et al. | 604/372 X |
| 4,834,087 | 5/1989 | Coleman et al. | 128/207.14 |
| 4,901,738 | 2/1990 | Brink et al. | 128/849 |
| 4,953,548 | 9/1990 | Stoddard et al. | 128/207.15 |
| 4,977,904 | 12/1990 | Kaufman | 128/156 X |
| 5,007,271 | 4/1991 | Boegli | 72/196 |
| 5,014,723 | 5/1991 | Kaufman | 128/849 X |
| 5,040,531 | 8/1991 | Coleman et al. | 128/207.15 X |

FOREIGN PATENT DOCUMENTS

| | | |
|---|---|---|
| 0139066 | 5/1985 | European Pat. Off. |
| 247797 | 12/1987 | European Pat. Off. ............... 128/849 |
| 8517084 | 11/1985 | Germany |
| 8800746 | 4/1988 | Germany |
| 8401294 | 4/1984 | WIPO |

OTHER PUBLICATIONS

Wrobel et al., Diffuse Laser Light Reflection from the Surfaces of Surgical Instruments, Published by Aescuap–Werke AG in West Germany in May, 1987.
Endotracheal Tube Safety During Laser Surgery, by Ray Fontenot, Jr., M.D. et al., Laryngoscope 97, Aug. 1987.

Primary Examiner—Robert A. Hafer
Assistant Examiner—Brian E. Hanlon
Attorney, Agent, or Firm—Ostrolenk, Faber, Gerb & Soffen

[57] ABSTRACT

Laser shields including the MEROCEL® brand hydroxylated polyvinyl acetal foam material, for covering an endotracheal tube, for covering parts of a patient's body, and for covering instruments and the like, and laser shields including a micro-corrugated metal foil layer.

52 Claims, 2 Drawing Sheets

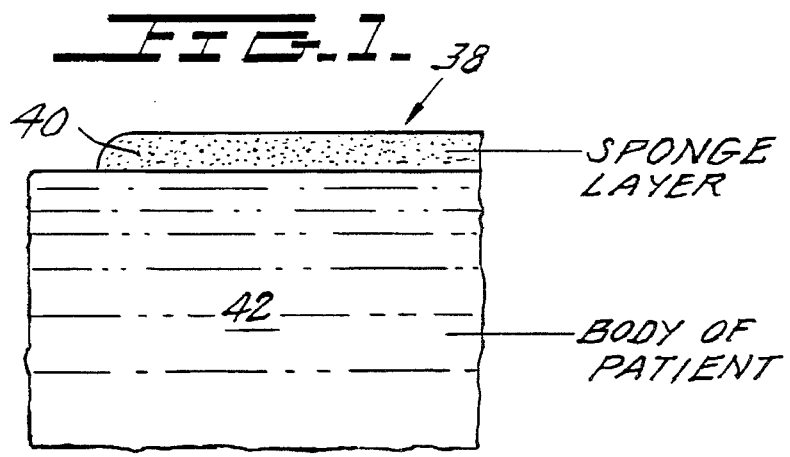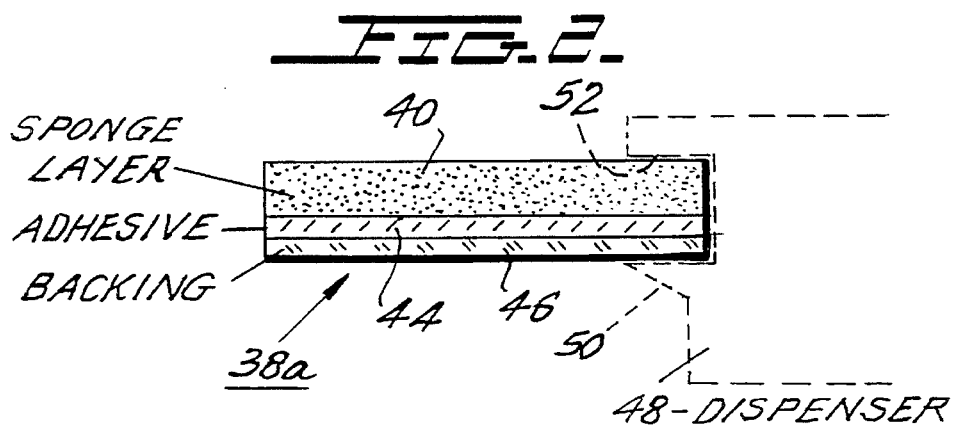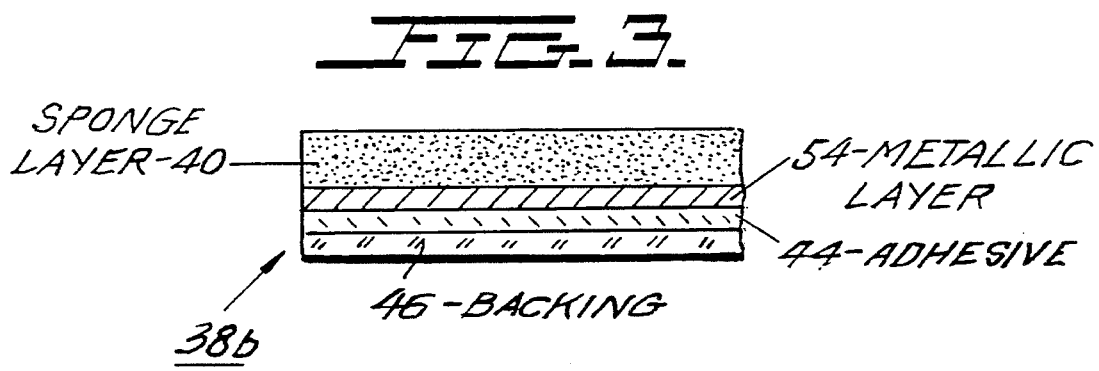

LASER SHIELD

This is a continuation of application Ser. No. 08/032,476, filed Mar. 16, 1993, now abandoned, which is a continuation of Ser. No. 07/259,790, filed Oct. 19, 1988, now abandoned.

BACKGROUND OF THE INVENTION

1. Field of the Invention

The invention relates to laser shields, for protecting patients and physicians from misdirected or reflected laser beams during laser surgery. More particularly, it relates to particular types of laser shields for covering an endotracheal tube, for covering parts of the body of a patient, and for covering instruments and the like.

2. Description of Related Art

Previously, surgical sponge-like materials and metallic shielding materials have each been used individually for protecting patients and physicians against misdirected and reflected laser beams during laser surgery. However, the known systems have had disadvantages.

For example, for protecting the patient's body it is known to use wet, sponge-type materials. U.S. Pat. No. 4,520,814 of Weeks and U.S. Pat. No. 4,616,641 of Teeple mention a practice of using wet towels or gauze as a laser shield. However, both patents indicate that the practice does not work well, and may be unsafe for various reasons.

U.S. Pat. No. 4,604,998 of Bellina, and the Teeple patent mentioned above, both disclose combinations of metallic and non-metallic layers as a laser barrier.

U.S. Pat. No. 4,601,286 of Kaufman discloses various articles which are intended to be impervious to misdirected or reflected laser beams, comprising a hydrophilic gel and optionally, additives such as salts, colorants or medications. The articles include dressings, drapes, tapes and tubes. An adhesive backing or a metallic sheet backing with a reflective mirror finish may also be provided. This system, too, has disadvantages, which will be discussed further hereinbelow.

The hazards of endotracheal tube fire or perforation of the endotracheal tube cuff during laryngeal laser surgery are described in Forttenor et al., "Endotracheal Tube Safety During Laser Surgery," Laryngoscope 97: 919–921, August 1987, the disclosures of which are incorporated by reference herein. The authors measured perforation times of saline-soaked cottonoid pledgers, such as Surgical Patties, manufactured by Codman & Shurtleff, Randolph, Mass., and determined that saline-soaked pledgers are very efficient for protecting endotracheal tube cuffs. They also evaluated the safety and ignition properties of red rubber, silicone, polyvinyl chloride, and Xomed Laser-Shield® tubes by studying their perforation times and ignition properties under controlled oxygen supply conditions. They concluded that the Xomed Laser-Shield® tube had the highest ignition threshold of the four tubes tested. This tube includes a metallic coating, which the authors theorized advantageously improves its ignition threshold. The metallic coating also has a dull surface which prevents reflected energy from injuring surrounding tissues.

Hatzenbuhler et al., U.S. Pat. No. 4,558,093, discloses a surgical sponge and an endotracheal tube made of a special material, in which densely packed bubbles, which may be water bubbles, are encapsulated in a matrix of silicone. This special material is intended to terminate laser radiation. In the sponge, a layer of the special material is covered on both sides by layers of conventional sponge material. In the endotracheal tube, the tube itself is made of the special material.

U.S. Pat. No. 4,632,108 of Geil, U.S. Pat. No. 4,611,588 of Laptewicz et al., U.S. Pat. No. 4,489,722 of Ferraro et al., and U.S. Pat. No. 4,520,814 of Weeks disclose materials having a laser reflective additive (such as metal) for use as a laser barrier for an endotracheal tube (see Geil and Ferraro et al.), or as a laser shield to be applied to parts of the body (see Laptewicz et al. and Weeks). Weeks also discloses a laser shield comprising a rubber pad, which has a laser-reflective coating thereon, and over that, an outer layer of surgical gauze which is kept damp to provide further laser protection.

Also currently in use by physicians are metal tapes and metallized plastic tapes with adhesive backing, for being spirally wrapped on an object which is to be protected. These tapes have serious disadvantages, such as their high reflectivity, which can cause hazardous reflection of laser beams. Further, gapping occurs between the edges of the tape wrapped on the object, which exposes the object to laser beams and exposes the patient to sharp edges which can cause trauma to delicate throat tissues.

The disclosures of the above materials are incorporated herein by reference.

SUMMARY OF THE INVENTION

In view of the dangers of laser surgery, and particularly laryngeal laser surgery, it is important to improve the level of protection provided by laser surgery shielding.

The present invention, as discussed below, provides significantly more effective laser shielding than the above-mentioned products. The invention employs the MEROCEL® surgical sponge material which is claimed and described in U.S. Pat. No. 4,098,728 of Rosenblatt, which is commonly assigned to the Americal Corp., Mystic, Conn., and the disclosures of which are incorporated herein by reference. MEROCEL® material is an expandable hydrophilic sponge material with exceptionally high liquid-holding capacity. It is biocompatible, non-toxic, lint-free, resilient, soft, non-abrasive and free of foreign leachable materials. It holds more water or saline than an equivalent weight of gauze and when burned, vaporizes without leaving residue, instead of igniting and leaving a residue as gauze would do.

MEROCEL® material, as discussed more fully in U.S. Pat. No. 4,098,728, comprises the reaction product of polyvinyl alcohol and formaldehyde, and may be referred to as hydroxylated polyvinyl acetal foam. More specifically, it may be referred to as hydroxylated polyvinyl formal foam. MEROCEL® material is an example of a non-gel-like hydrophilic polymer foam. Other high-water-content materials which are analogous to some extent are the hydrogels, such as hydroxyethylmethacrylic acid-type polymers, acrylonitrile-acrylamide, which is disclosed in the Kaufman patent cited above, and various other gel-like materials.

These hydrophilic gel-like polymers would be usable to a degree, but MEROCEL® material is superior to the hydrogel materials, in its tensile strength, elongation, softness, freedom from residues upon ignition, wicking properties, and suitability as a substrate for applying topical anesthetic jellies. These advantages of MEROCEL® material will be discussed further hereinbelow.

The present invention protects a patient against misdirected laser beams during laser surgery by employing MEROCEL® material by itself or in combination with a foil-as a laser shield. The MEROCEL® material may have an optional adhesive backing to secure the sponge to the surface of the patient. MEROCEL® material provides overall significantly superior protection against laser beams, far exceeding that of the prior art systems. MEROCEL® material is advantageous because it holds more water than the prior art sponge systems, of cotton, rayon, cellulose, gauze, or their combinations, and thereby absorbs more laser energy than other sponge-like materials. This makes the above-mentioned multi-layer materials and/or laser-resistant backing materials unnecessary. Furthermore, MEROCEL® material does not burn if overheated by laser energy. Rather, it melts and vaporizes, without leaving carbonaceous combustion residues, which is less contaminating and thereby provides an increased margin of safety for the patient. It also will not fragment, which would introduce lint into the body of a patient.

The invention also relates to a laser-resistant covering for an endotracheal tube. This covering comprises a layer of MEROCEL® material which is backed with a metal foil and an adhesive, wrapped around an endotracheal tube to protect the tube against scattered laser beams, which otherwise may penetrate the tube during laser surgery. This covering provides two lines of defense against laser penetration. The MEROCEL® material layer absorbs lesser laser contacts. If an extended laser contact should vaporize the MEROCEL® material layer, then the second line of defense, namely the foil, comes into play. The metal foil layer is advantageously micro-corrugated. For example, the foil material may be worked by an opposed gear arrangement so as to have micro-corrugations which are about 1 mm deep and have peaks spaced about 1 mm apart. The foil material is also dead-soft annealed so as to be formable with substantially no resiliency. These features make the foil layer substantially non-reflective and give it extremely advantageous mechanical and elongation properties. The corrugations also provide stretchability and thereby improve the flexibility of the tube.

The invention also relates to a protective material provided in the form of a tape and which may be supplied from a dispenser or the equivalent. The tape material comprises MEROCEL® material and may also comprise an adhesive backing, a metallic shield layer, or both.

The invention further relates to a laser shield comprising, in combination, a layer of a hydrophilic material and a micro-corrugated foil layer.

Unlike the prior art systems, a laser shield according to the present invention absorbs energy, rather than simply reflecting energy, which does not eliminate laser reflection hazards. MEROCEL® material is more energy-absorptive than other materials, since it holds more fluid than conventional sponge-like materials, and thereby constitutes a more effective laser barrier.

The advantages of the present invention are totally unexpected in view of the above-mentioned prior art. Hatzenbuhler et al. requires the use of Hatzenbuhler et al.'s special material, to form a sponge-type laser shield. Although Weeks, Teeple and Hatzenbuhler et al. may mention the use of a conventional sponge material by itself as a laser shield, they also suggest this had disadvantages, so the prior art, considered as a whole, actually teaches away from any such sponge-like shield. Prior art hydrophilic gels or sponge-like shields, not supplemented by a laser-resistant metal backing or the like, have not been satisfactory in themselves. On the contrary, the use of the MEROCEL® material for this purpose, as disclosed and claimed herein, gives surprising and unexpected advantages.

The micro-corrugated foil layer disclosed herein is advantageous in itself, particularly when combined with a layer of a hydrophilic material.

As an endotracheal tube protector, the metal-backed MEROCEL® material is also unknown in the art, and provides superior performance in absorbing energy. The tape material is also unknown and provides further advantages.

BRIEF DESCRIPTION OF THE DRAWINGS

These and other objects, features and advantages of the invention will be further explained in connection with the following detailed description of embodiments of the invention, taken together with the drawings, in which:

FIG. 1 is a cross-sectional schematic view showing a laser shield applied to the body of a patient;

FIG. 2 is a cross-sectional schematic view showing a multi-layer tape-type laser shield contained in a dispenser;

FIG. 3 is a cross-sectional schematic view showing another multi-layer laser shield which includes a metallic layer;

DETAILED DESCRIPTION OF PREFERRED EMBODIMENTS OF THE INVENTION

Figure 4:
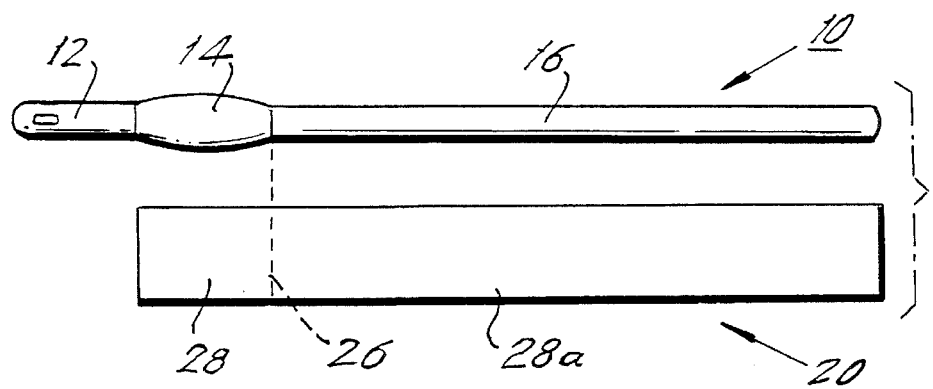
FIG. 4 is a simplified plan view showing an endotracheal tube and a laser shield for being applied thereto.

FIG. 1 is a schematic cross-sectional view showing a laser shield 38 which comprises a sponge layer 40 comprising MEROCEL® material, located for protecting a portion 42 of the body of a patient during laser surgery. As shown in FIG. 2, a laser shield 38a may also comprise an adhesive layer 44 for adhering the laser shield to the patient, and a non-adhesive backing 46 of silicone paper or the equivalent may also be provided, as is well known.

When impregnated with saline or water, such a laser shield 38 or 38a will withstand up to 5 watts of energy from a $CO_2$ laser for up to 3 seconds. The shield can be applied either to the patient directly or to a drape. The sponge layer 40 should be as thick as practicable. A 1-inch sponge layer holds four times as much water as a ¼-inch layer, and has correspondingly greater laser-resistive power.

The laser shield 38a may be provided in the form of a tape. As shown schematically in FIG. 2, the tape-type laser shield 38a is contained in a dispenser 48 of any conventional type. The dispenser 48 may have a cutting edge 50 adjacent to a dispensing slot 52. Such a tape-type laser shield is especially useful for covering specular surfaces of surgical instruments, from which laser beams might otherwise be reflected. For this purpose a width of 1 to 2 inches is especially advantageous. The tape-type laser shield is also useful for protecting limited areas of the patient's body.

A tape-type or non-tape-type laser shield 38b having even greater laser-resistive power may be obtained by providing a metallic layer 54, as seen in FIG. 3.

As an alternative, a non-adhesive connector such as an elastic band can be attached to a laser shield to hold the laser shield to part of the patient's body, for example the eyes. Such a laser shield also preferably has a laser-reflective metal foil layer.

It should be noted that the Figures herein are not drawn to scale and do not necessarily accurately represent the thicknesses of the various layers shown therein. The various layers may be multiplied or provided in a different order. Any suitable means, such as conventional adhesives, may be employed for adhering the various layers together.

Figure 5:
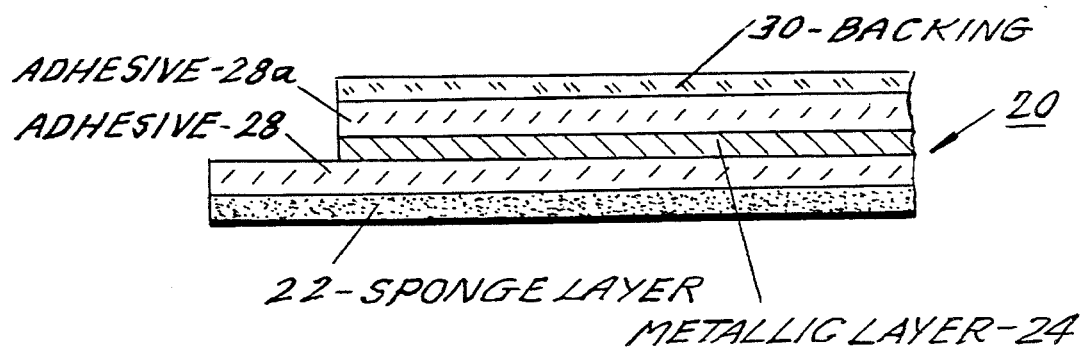
FIG. 5 is a schematic cross-sectional view of the laser shield of FIG. 4.

Referring now to FIGS. 4 and 5, an endotracheal tube protector according to the invention will be described. A conventional endotracheal (ET) tube 10 includes a first end 12, a balloon cuff 14, and a second end 16. The tube may be a conventional endotracheal tube made of red rubber, for example. An embodiment of a laser shield 20 for the endotracheal tube 10 comprises a MEROCEL® material sponge layer 22 and an adhesive layer 28 thereon, which are sized and shaped to be wrapped 360° around the second end of the endotracheal tube and the balloon cuff, with a slight overlap. However, the shield is not wrapped around the first end of the ET tube.

Alternatively, the laser shield 20 may extend only to the line of demarcation 26 between the cuff 14 and the second end 16. Pledgers made of MEROCEL® material, or less preferably cotton or the like, then should be provided to pack and protect the endotracheal tube cuff.

Also shown is a metallic layer 24 comprising a micro-corrugated fine silver foil. The silver foil 24 is bonded to the MEROCEL® material layer 22 by the adhesive layer 28 and is sized and shaped to be wrapped around the second end of the endotracheal tube, up to a line of demarcation 26 which is defined between the second end 16 and the balloon cuff 14. The silver foil portion 24 should not cover the balloon cuff 14, because the cuff must remain inflatable and free to expand to seal the trachea. Any foil with high heat conductivity may be used if it does not corrode and is in no other respect non-biocompatible.

A preferred form of the silver foil material is (a) of fine-grade purity with 99.9 percent minimum silver content; (b) pinhole-free to provide a complete laser barrier; (c) micro-corrugated to allow for flexibility and some beam diffusion; and (d) dead-soft annealed for bending without any cracking.

Overlying the silver foil layer 24 is a second adhesive layer 28a. A protective silicone paper layer 30 protects the adhesive layer 28a, but is easily removable to expose the adhesive layer 28a for use. Of course, the paper layer 30 may also cover the exposed portion of the adhesive layer 28 (see FIG. 4).

In use, the endotracheal tube laser shield is placed on a flat surface, for example with the silicone protective paper layer 30 face up. The silicone protective paper layer 30 is peeled off, uncovering the adhesive layer 28. The endotracheal tube 10 is placed along the center of the adhesive layer, while lining up the end of the metal layer 24 with the demarcation line 26 between the balloon cuff 14 and the second end 16. While the tube 10 is maintained in a flattened orientation adhered to the center of the strip, the shield is wrapped by rolling it around the tube 10 on both sides and firmly pressed in place around the endotracheal tube 10.

Advantageously, there will be approximately 1/16-inch of overlap of the circumference of the laser shield along the length of the tube 10. This is preferable, because total shielding of the endotracheal tube is essential. After the shield 20 is in place, the tube may be bent to the desired curvature in the usual way. Then it should be inspected to ensure that all of the edges of the shield 20 remain firmly attached. Finally, the layer 22 is saturated with saline and may be coated with an anesthetic or lubricant jelly and then may be introduced normally in the patient for carrying out the surgery.

Alternatively, if tracheal tube space for intubation is limited, the diameter of the covered tube can be reduced by coating with anesthetic or lubricant jelly only. The diameter of the shielded tube is reduced when it is not hydrated before insertion.

In all of these arrangements, the layer 22 should be kept saturated with saline during use, to maximize its advantageous laser-energy-resisting functions.

EXAMPLE

This example of an endotracheal (ET) tube laser shield provides 360° of superior, cost-effective, protection against penetration from a $CO_2$ laser beam or from other lasers from which safe and convenient protection is beneficial. It comprises a laminate of fiber-free MEROCEL® material backed with pure, corrugated, silver foil. It easily adheres to plastic, rubber, and PVC ET tubes by a hypoallergenic, pressure-sensitive, adhesive coating on the silver foil. When the MEROCEL® material is saturated with saline or water, it provides additional protection from accidental penetration by the laser beam, while providing a soft, moist interface with the mucosa. The ET tube may also be packed and protected by MEROCEL® material pledgers. The pledgers may also be laminates, such as MEROCEL® material/metal foil/MEROCEL® material, for additional protection.

This ET tube laser shield withstands 30 watts of continuous laser energy (0.8 mm beam width) for three minutes with 100% oxygen present. It is a cost-effective alternative to the more expensive laser protective devices. It can be used with any size of plastic, rubber, and PVC ET tubes. Its micro-corrugated silver foil layer provides rapid heat dissipation and diffuses beam reflections. Its sponge layer surface maintains a non-traumatic interface with tissues, reducing post-operative irritation, and the sponge surface also diffuses beam reflections.

There are three levels of protection: (1) The sponge saturates with fluid and provides a barrier to the laser, and a cooling effect to the tissue. (2) Also, the silver foil is highly conductive and dissipates heat rapidly to the moist, cooling sponge material. This cooling effect on the silver foil emanates from the rapid wicking properties of the MEROCEL® foam, which can rapidly transfer moisture to eliminate any hot spots on the metal foil surface. This is superior to gel-like materials, which do not have any internal moisture transfer and cannot eliminate a hot spot. (3) The silver foil is micro-corrugated to reduce the possibility of any focused beam reflections from the surface of the foil.

Additionally, the ET tube may be curved without kinking, after the shield is in place. The sponge also provides an improved surface upon which to apply anesthesia jelly for more effective topical anesthesia. MEROCEL® material contains no fibers that can flush into the operative site. If the MEROCEL® sponge material is exposed to a laser beam after being allowed to dry out, it will not produce carbon particles as cotton or rayon would. MEROCEL® material vaporizes instead of producing residues.

Endotracheal (ET) tube laser shields according to this embodiment of the invention were tested. Following is a summary of the results of the study.

Materials Tested

1. Pure aluminum foil
2. Pure copper foil
3. Pure silver foil
4. 303 grade stainless steel foil 5. MEROCEL® surgical sponge material—hydrophilic interface 6. Hypoallergenic pressure sensitive adhesive.

Conditions of Test

All foils were approximately 1 mil thick.

All testing was done on both the metal by itself and the MEROCEL® material/metal laminate.

The MEROCEL® sponge material portion was 1 mm in thickness laminated to the 1 mil metal foil with a waterproof hypoallergenic adhesive.

All wraps were on PVC tubes.

All shields were tested for a 3 minute duration with a $CO_2$ laser continuous wave at 100% oxygen.

All shields were tested at 30 watts.

Beam width at focal point was 0.8 mm.

The temperature rise of the shield was measured with a thermocouple placed 1 cm from the beam impact point to measure the temperature rise.

Results

The temperature rise on the PVC tubes was the following:

Aluminum 46.8° C.

Copper 68.6° C.

Silver 50°–60° C.

One silver trial gave a temperature rise to 95° C., and one trial on the seam registered 155.9° C.

All of the above metals by themselves and in combination with the MEROCEL® sponge material were found to be non-penetrable at 30 watts for 3 minutes continuous wave at 100% oxygen, 0.8 mm beam width.

The stainless was penetrable at 32–82 seconds when wrapped around the tube, and penetrable in less than 1 second when tested separately at 30 watts.

All the foils were found to be highly reflective.

Notes

1. Temperature rise indicates rate of heat conductivity away from the beam contact point, which relates directly to heat dissipation from the site.

2. After these tests had been made, increased beam diffusion from the surface was accomplished by altering the surface of the foil by micro-corrugating. The preferred material is corrugated silver foil. The silver foil can be further altered to increase its beam diffusivity, if required, by chemical etching or sandblasting, or by reacting with chemical agents such as sulfides to cause a dull, darkened surface coloration.

Although illustrative embodiments of the invention have been described herein, the appended claims are not limited to those embodiments but are to be construed as including within their scope all modifications and alternatives that may occur to one of ordinary skill in the art which fairly fall within the teachings set forth hereinabove.

What is claimed is:

1. A method of protecting the body of a patient from laser injury during laser surgery, comprising the steps of:

determining a surface which may receive laser radiation and thereby injure said patient during said surgery;

applying a sheet of hydrophilic surgical sponge material comprising polyvinyl acetal foam to said surface; and applying a layer of a laser-reflective metal foil which is corrugated so as to increase its flexibility, stretchability, and laser-beam diffusivity, between said sponge material sheet and said surface.

2. A method as in claim 1, further comprising the steps of:

substantially saturating said sponge material with a liquid; and remoistening said sponge material as necessary to maintain substantial saturation thereof during said surgery.

3. A method as in claim 1, wherein said sponge material and metal foil layer are applied to said surface by applying an adhesive layer to the metal foil layer, and adhering said adhesive layer to said surface.

4. A method as in claim 3, further comprising the steps of providing said surgical sponge sheet material, foil layer, and adhesive layer in the form of a tape and containing said tape in a tape dispenser.

5. A method as in claim 1, further comprising the step of making said metal foil layer from copper.

6. A method as in claim 1, further comprising the step of microcorrugating said metal foil layer.

7. A method as in claim 6, further comprising the step of dead-soft annealing said metal foil layer.

8. A method as in claim 6, wherein said metal foil layer is micro-corrugated by working the foil material between opposed gears.

9. A method as in claim 1, further comprising chemically treating said metal foil layer by chemical etching or a chemical reaction to further enhance its diffusivity.

10. A method of protecting an endotracheal tube comprising a first end and a second end, and a balloon cuff intermediate said first and second ends, from laser injury during laser surgery, comprising the steps of:

placing a metal foil layer around said second end of said tube, said metal foil layer being corrugated so as to increase its flexibility, stretchability, and laser-beam diffusivity;

placing a layer of hydrophilic surgical sponge material comprising hydroxylated polyvinyl acetal foam around said metal foil layer;

substantially saturating said sponge material by applying a liquid; and reapplying said liquid as necessary to maintain substantial saturation of said sponge material during the surgery.

11. A method as in claim 10, wherein said sponge layer and said metal foil layer are bonded together.

12. A method as in claim 11, wherein said sponge layer is also placed around said cuff.

13. A method as in claim 11, wherein said sponge layer and said foil layer are adhered to said tube by an adhesive.

14. A method as in claim 10, wherein said metal foil layer is not placed around said balloon cuff of said endotracheal tube.

15. A method as in claim 14, wherein said metal foil layer is bonded to an end portion of said sponge layer such that the metal foil layer is placed on the second end of the endotracheal tube, but not on the balloon cuff.

16. A method as in claim 10, wherein said metal foil layer is not placed on said cuff of said endotracheal tube, while said sponge layer comprising polyvinyl acetal foam is placed on both said second end and said cuff.

17. A method as in claim 10, further comprising the step of making said metal foil layer from copper.

18. A method as in claim 10, further comprising the step of micro-corrugating said metal foil layer.

19. A method as in claim 18, wherein said metal foil layer is micro-corrugated by working the foil material between opposed gears.

20. A method as in claim 10, further comprising chemically treating said metal foil layer to enhance its laser-beam diffusivity.

21. A method as in claim 20, wherein said metal foil layer is chemically etched.

22. A method as in claim 20, wherein said metal foil layer is treated with a chemical agent to cause a dull, darkened surface coloration.

23. A method as in claim 20, further comprising the step of micro-corrugating said metal foil layer.

24. A method as in claim 10, further comprising the step of sandblasting said metal foil layer to enhance its diffusivity.

25. A method as in claim 24, further comprising the step of micro-corrugating said metal foil layer.

26. A method as in claim 18, 23 or 25, wherein said metal foil layer has substantially 1 mm corrugations.

27. A method as in claim 18, 23 or 25, wherein said metal foil layer is dead-soft annealed.

28. A method as in claim 10, further comprising the steps of:

forming said metal foil layer and said sponge layer substantially in the shape of an elongated rectangle having a pair of opposite long sides and a pair of opposite short sides; and forming said metal foil and sponge layer into the general shape of an elongated cylinder on said endotracheal tube by wrapping said metal foil layer and said sponge layer around the endotracheal tube in a direction substantially parallel to said short sides and transverse to said long sides.

29. A laser shield for an endotracheal tube comprising a first end and a second end, and a balloon cuff intermediate said first and second ends, said laser shield comprising:

an elongated hydrophilic surgical sponge layer comprising polyvinyl acetal foam, sized and shaped to be placed upon and thereby substantially cover the second end of said tube;

an elongated metal foil layer at least partially overlying said sponge layer and sized and shaped to be placed upon and thereby substantially cover said second end, said metal foil layer being corrugated so as to increase its flexibility, stretchability, and laser-beam diffusivity; and means for securing said layers to said endotracheal tube.

30. A laser shield as in claim 29, wherein said securing means comprises adhesive material overlying said metal foil layer and overlying any portion of said sponge layer which is not overlaid by said metal foil layer.

31. A laser shield as in claim 29, wherein said metal foil layer is sized and shaped not to overlie said balloon cuff when said shield is wrapped upon said endotracheal tube, the balloon cuff being substantially covered by a portion of the sponge layer which is not overlaid by the metal foil layer.

32. A laser shield as in claim 29, wherein said metal foil layer is bonded to said sponge layer.

33. A laser shield as in claim 32, wherein said sponge layer is sized and shaped also to overlie said cuff.

34. A method as in claim 29, wherein said metal foil layer from copper.

35. A laser shield as in claim 29, wherein said metal foil layer is micro-corrugated.

36. A laser shield as in claim 29, wherein said metal foil is chemically treated and thereby has enhanced laser-beam diffusivity.

37. A method as in claim 36, wherein said metal foil layer is chemically etched.

38. A laser shield as in claim 36, wherein said metal foil layer is treated with a chemical agent to cause a dull, darkened surface coloration.

39. A laser shield as in claim 36, wherein said metal foil layer is micro-corrugated.

40. A laser shield as in claim 29, wherein said metal foil layer is sandblasted and thereby has enhanced diffusivity.

41. A laser shield as in claim 40, wherein said metal foil layer is micro-corrugated.

42. A laser shield as in claims 35, 39 or 41, wherein said metal foil layer is micro-corrugated with substantially 1 mm corrugations.

43. A laser shield as in claims 35, 39 or 41, wherein said metal foil is dead-soft annealed.

44. A laser shield as in claim 29, wherein said metal foil layer and said sponge layer are each formed substantially in the shape of an elongated rectangle having a pair of opposite long sides and a pair of opposite short sides, such that said laser shield can be formed into the general shape of an elongated cylinder on said endotracheal tube by being wrapped around the endotracheal tube in a direction substantially parallel to said short sides and transverse to said long sides.

45. A method of shielding an object from laser beams during laser surgery, comprising the steps of:

applying a microcorrugated heat-conductive metal foil layer to said object;

applying a layer of a hydrophilic polyvinyl acetal foam surgical sponge material to said object over said metal foil layer; and substantially saturating said hydrophilic material with a liquid.

46. A method as in claim 45, wherein said heat-conductive metal foil layer is micro-corrugated so as to increase its flexibility, stretchability, and laser-beam diffusivity.

47. A method as in claim 46, further comprising forming a laminate comprising said hydrophilic material layer and metal foil layer and an adhesive therebetween; and applying said laminate to said object.

48. A method as in claim 46, wherein said metal foil is dead-soft annealed.

49. A laser shield for shielding an object from laser beams during laser surgery, comprising:

a microcorrugated heat-conductive metal foil layer; and a corresponding layer of a hydrophilic polyvinyl acetal foam surgical sponge material over said metal foil layer;

said layers being sized and shaped for jointly shielding said object.

50. A laser shield as in claim 49, wherein said heat-conductive metal foil layer is micro-corrugated so as to be flexible, stretchable and laser-beam diffusive.

51. A laser shield as in claim 50, further comprising an adhesive layer disposed between said hydrophilic material layer and said metal foil layer.

52. A laser shield as in claim 50, wherein said metal foil is dead-soft annealed.

\* \* \* \* \*